United States Patent
Levin et al.

(10) Patent No.: US 7,485,667 B2
(45) Date of Patent: Feb. 3, 2009

(54) ACETYLENIC ARYL SULFONATE HYDROXAMIC ACID TACE AND MATRIX METALLOPROTEINASE INHIBITORS

(75) Inventors: Jeremy Ian Levin, New City, NY (US); Mila Ti Du, Cumming, GA (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 11/709,437

(22) Filed: Feb. 21, 2007

(65) Prior Publication Data

US 2007/0155834 A1 Jul. 5, 2007

Related U.S. Application Data

(62) Division of application No. 10/739,304, filed on Dec. 19, 2003, now Pat. No. 7,199,155.

(60) Provisional application No. 60/436,088, filed on Dec. 23, 2002.

(51) Int. Cl.
*A61K 31/255* (2006.01)
*C07C 309/75* (2006.01)

(52) U.S. Cl. .................................................... 514/518

(58) Field of Classification Search .................. None
See application file for complete search history.

(56) References Cited

U.S. PATENT DOCUMENTS

| | | |
|---|---|---|
| 5,455,258 A | 10/1995 | MacPherson et al. |
| 5,506,242 A | 4/1996 | MacPherson et al. |
| 5,552,419 A | 9/1996 | MacPherson et al. |
| 5,753,653 A | 5/1998 | Bender et al. |
| 5,770,624 A | 6/1998 | Parker |
| 5,804,593 A | 9/1998 | Warpehoski et al. |
| 5,817,822 A | 10/1998 | Nantermet et al. |
| 5,866,587 A | 2/1999 | De Nanteuil et al. |
| 5,929,097 A | 7/1999 | Levin et al. |
| 5,962,481 A | 10/1999 | Levin et al. |
| 5,977,408 A | 11/1999 | Levin et al. |
| 6,162,814 A | 12/2000 | Levin et al. |
| 6,162,821 A | 12/2000 | Levin et al. |
| 6,197,795 B1 | 3/2001 | Levin et al. |
| 6,200,996 B1 | 3/2001 | Levin et al. |
| 6,207,672 B1 | 3/2001 | Thorwart et al. |
| 6,225,311 B1 | 5/2001 | Levin et al. |
| 6,228,869 B1 | 5/2001 | Levin et al. |
| 6,277,885 B1 | 8/2001 | Levin et al. |
| 6,313,123 B1 | 11/2001 | Levin et al. |
| 6,326,516 B1 | 12/2001 | Levin et al. |
| 6,753,337 B2 * | 6/2004 | Levin et al. ............ 514/330 |
| 6,946,473 B2 * | 9/2005 | Levin et al. ............ 514/301 |

FOREIGN PATENT DOCUMENTS

| | | |
|---|---|---|
| DE | 19542189 A1 | 5/1997 |
| EP | 0 606 046 A1 | 7/1994 |
| EP | 0 757 037 A2 | 2/1997 |
| EP | 0 757 984 A1 | 2/1997 |
| EP | 0 803 505 A1 | 10/1997 |
| EP | 0 915 086 A1 | 5/1999 |
| EP | 0 950 656 A1 | 10/1999 |
| WO | WO 95/35275 | 12/1995 |
| WO | WO 95/35276 | 12/1995 |
| WO | WO 96/00214 | 1/1996 |
| WO | WO 96/27583 | 9/1996 |
| WO | WO 96/33172 | 10/1996 |
| WO | WO 97/18194 | 5/1997 |
| WO | WO 97/19068 | 5/1997 |
| WO | WO 97/20824 | 6/1997 |
| WO | WO 97/22587 | 6/1997 |
| WO | WO 97/27174 | 7/1997 |
| WO | WO 97/45402 | 12/1997 |
| WO | WO 98/03166 | 1/1998 |
| WO | WO 98/07697 | 2/1998 |
| WO | WO 98/08815 | 3/1998 |
| WO | WO 98/08822 | 3/1998 |
| WO | WO 98/08823 | 3/1998 |
| WO | WO 98/08825 | 3/1998 |
| WO | WO 98/08827 | 3/1998 |
| WO | WO 98/08853 | 3/1998 |
| WO | WO 98/16503 | 4/1998 |
| WO | WO 98/16506 | 4/1998 |
| WO | WO 98/16514 | 4/1998 |
| WO | WO 98/16520 | 4/1998 |
| WO | WO 98/27069 | 6/1998 |
| WO | WO 98/31664 | 7/1998 |

(Continued)

OTHER PUBLICATIONS

Tsuchiya, S., et al., Int. J. Cancer, 26, pp. 171-176, (1980).

(Continued)

*Primary Examiner*—Fiona T Powers
(74) *Attorney, Agent, or Firm*—Pepper Hamilton LLP

(57) ABSTRACT

Hydroxamic acids having the formula

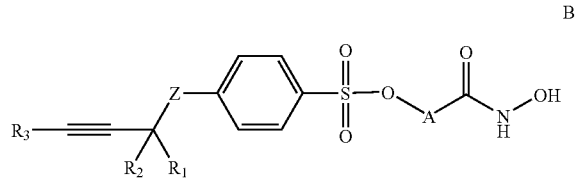

are useful in treating disease conditions mediated by TNF-α, such as rheumatoid arthritis, graft rejection, cachexia, inflammation, fever, insulin resistance, septic shock, congestive heart failure, inflammatory disease of the central nervous system, inflammatory bowel disease or HIV infection.

11 Claims, No Drawings

FOREIGN PATENT DOCUMENTS

| | | |
|---|---|---|
| WO | WO 98/33768 | 8/1998 |
| WO | WO 98/34918 | 8/1998 |
| WO | WO 98/39313 | 9/1998 |
| WO | WO 98/39315 | 9/1998 |
| WO | WO 98/39329 | 9/1998 |
| WO | WO 98/42659 | 10/1998 |
| WO | WO 98/43963 | 10/1998 |
| WO | WO 99/18074 | 4/1999 |
| WO | WO 00/09492 | 2/2000 |
| WO | WO 00/32570 | 6/2000 |
| WO | WO 00/35885 | 6/2000 |
| WO | WO 00/44709 | 8/2000 |
| WO | WO 00/44710 | 8/2000 |
| WO | WO 00/44711 | 8/2000 |
| WO | WO 00/44713 | 8/2000 |
| WO | WO 00/44716 | 8/2000 |
| WO | WO 00/44723 | 8/2000 |
| WO | WO 00/44730 | 8/2000 |
| WO | WO 00/44740 | 8/2000 |
| WO | WO 00/44749 | 8/2000 |
| WO | WO 00/59285 | 10/2000 |
| WO | WO 01/10827 A1 | 2/2001 |
| WO | WO 01/27084 A1 | 4/2001 |

OTHER PUBLICATIONS

Old, Lloyd, J., Science, 230, pp. 630-632, (1985).
Piquet, P.F., et al., J. Exp. Med., 166, pp. 1280-1289, (1987).
Beutler, B., et al., Ann. Rev. Biochem 57, pp. 505-518, (1988).
Mathison, J.C., et al., J. Clin. Invest. 81, pp. 1925-1937 (1988).
Greene, T.W., Wuts, P.G.M., "Protective Groups in Organic Synthesis" 2nd Edition, Wiley & Sons, New York (1991).
Gatanaga, T., et al., Cellular Immunology 138, pp. 1-10, (1991).
Miethke, T., et al., J. Exp. Med. 175, pp. 91-98, (1992).
Peterson, P.K., et al., J. Clin. Invest. 89, pp. 574-580, (1992).
Hotamisligil, G.S., et al., Science, 259, pp. 87-91, (1993).
Bjornberg, F., et al., Lymphokine Cytokine Res. 13, pp. 203-211, (1994).
Rankin, E.C., et al., Br. J. Rheumatol 34, pp. 334-342, (1995).
Pallares-Trujillo, J., et al., Med. Res. Reviews 15(6), pp. 533-546, (1995).
Ferrari, R., et al., Circulation 92(6), 1479, pp. 1-12 (1995).
Packer, M., Circulation 92(6), 1379, pp. 1-8, (1995).
McGeehan, Gerard M., et al., Current Pharmaceutical Design 2, pp. 662-667 (1996).
Pharmaprojects, Therapeutic Updates 17 (Oct.), au197 M2Z, (1996).
MacPherson, L.J., J. Med. Chem 40, pp. 2525-2532, (1997).
Isomaki, P., et al., Ann. Med. 29, pp. 499-507, (1997).
Grossman, J.M., et al., Journal of Women's Health 6(6), pp. 627-638, (1997).
SCRIP 2349, pp. 20-21, (1998).
Xue, C.B., et al., J. Med. Chem. 41, pp. 1745-1748, (1998).
Lowe, C., et al., Exp. Opin. Ther. Patents 8, pp. 1309-1322, (1998).
Ksontini, R., et al., Arch. Surg. 133, pp. 558-567, (1998).
Camussi, G., et al., Drugs 55(5), pp. 613-620, (1998).
Shire, M.G., et al., Exp. Opin. Ther. Patents 8(5), pp. 531-544, (1998).
Pikul, S., et al., J. Med. Chem 41, pp. 3568-3571, (1998).
Levin, J.I., et al., Bioorg. Med. Chem. Letters 8, pp. 2657-2662, (1998).
Tamura, Y., et al., J. Med. Chem. 41, pp. 640-649, (1998).
Michaelides, M.R., et al., Curr. Pharm. Design 5, pp. 787-819, (1999).
Barlaam, B., et al., J. Med. Chem. 42, pp. 4890-4908, (1999).
Cherney, R.J., et al., Bioorg. Med. Chem. Lett. 9, pp. 1279-1284, (1999).
Newton, R.C., et al., J. Med. Chem. 42, pp. 2295-2314, (1999).
Nelson, F.C., et al., Exp. Opin. Invest. Drugs 8, pp. 383-392, (1999).
Holms, J., et al., Bioorg. Med. Chem. Lett. 11, pp. 2907-2910, (2001).
Levin, J.I., et al., Bioorg. Med. Chem. Lett. 11, pp. 235-238, (2001).
Levin, J.I., et al., Bioorg. Med. Chem. Lett. 11, pp. 239-242, (2001).
Levin, J.I., et al., Bioorg. Med. Chem. Lett. 11, pp. 2189-2192, (2001).
Levin, J.I., et al., Bioorg. Med. Chem. Lett. 11, pp. 2975-2978, (2001).
Skiles, J.W., et al., Curr. Med. Chem. 8, pp. 425-474, (2001).
Rabinowitz, M.H., et al., J. Med. Chem. 44, pp. 4252-4267, (2001).
Xue, C.B., et al., J. Med. Chem. 44, pp. 2636-2660, (2001).
Letavic, M.A., et al., Bioorg. Med. Chem. Lett. 12, pp. 1387-1390, (2002).
Levin, J.I., et al., Bioorg. Med. Chem. Lett. 12, pp. 1199-1202, (2002).
Chen, J.M., et al., Bioorg. Med. Chem. Lett. 12, pp. 1195-1198, (2002).
Duan, J.J., et al., J. Med. Chem. 45, pp. 4954-4957, (2002).
Beck, G., et al., J. Pharmacol. Exp. Ther. 302, pp. 390-396, (2002).
Kottirsch, G., et al., J. Med. Chem. 45, pp. 2289-2293, (2002).

* cited by examiner

ACETYLENIC ARYL SULFONATE HYDROXAMIC ACID TACE AND MATRIX METALLOPROTEINASE INHIBITORS

This application is a divisional application of copending application, application Ser. No. 10/739,304 filed Dec. 19, 2003 which claims priority from provisional application, Application No. 60/436,088 filed on Dec. 23, 2002. These applications are herein incorporated by reference in their entireties.

FIELD OF INVENTION

The present invention relates to acetylenic aryl sulfonate hydroxamic acids which act as inhibitors of TNF-α converting enzyme (TACE) and matrix metalloproteinases (MMP), to processes for the preparation of such compounds, and to pharmaceutical compositions comprising such compounds. The compounds of the present invention are useful in disease conditions mediated by TNF-α, such rheumatoid arthritis, graft rejection, cachexia, inflammation, fever, insulin resistance, septic shock, congestive heart failure, inflammatory disease of the central nervous system, inflammatory bowel disease, or HIV infection.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. *J. Women's Health* 1997, 6(6), 627; Isomaki, P.; Punnonen, *J. Ann. Med.* 1997, 29, 499; Camussi, G.; Lupia, E. *Drugs,* 1998, 55(5), 613-620.] septic shock [Mathison, et. a.l *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505-518.], anorexia, inflammation [Ksontini, R.; MacKay, S. L. D.; Moldawer, L. L. *Arch. Surg.* 1998, 133, 558-567.], congestive heart failure [Packer, M. *Circulation,* 1995, 92(6), 1379; Pages 1-8; Ferrari, R.; Bachetti, T.; et. al. *Circulation,* 1995, 92(6), 1479, 1-12.], post-ischaemic reperfusion injury, inflammatory disease of the central nervous system, inflammatory bowel disease, insulin resistance [Hotamisligil, G. S.; Shargill, N. S.; Spiegelman, B. M.; et. al. *Science,* 1993, 259, 87-91.] and HIV infection [Peterson, P. K.; Gekker, G.; et. al. *J. Clin. Invest* 1992, 89, 574-580; Pallares-Trujillo, J.; Lopez-Soriano, F. J. Argiles, J. M. *Med. Res. Reviews,* 1995, 15(6), 533-546.]], in addition to its well-documented antitumor properties [Old, L. *Science,* 1985, 230, 630-632.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. *Br. J. Rheumatol.* 1995, 34, 334-342; *Pharmaprojects,* 1996, Therapeutic Updates 17 (October), au197-M2Z.]. This observation has recently been extended to humans as well as described in "TNF-α in Human Diseases", *Current Pharmaceutical Design,* 1996, 2, 662-667.

It is expected that small molecule inhibitors of TACE would have the potential for treating a variety of disease states [Nelson, F. C.; Zask, A. *Exp. Opin. Invest. Drugs* 1999, 8, 383-392; Lowe, C. *Exp. Opin. Ther. Patents* 1998, 8, 1309-1322; Newton, R. C.; Decicco, C. P. *J. Med. Chem.* 1999, 42, 22952314.]. Although a variety of TACE inhibitors are known, many of these molecules are peptidic and peptide-like [Cherney, R. J.; Wang, L.; Meyer, D. T.; et. al. *Bioorg. Med. Chem. Lett.,* 1999, 9, 1279-1284; Xue, C.-B.; He, X.; Roderick, J. *J. Med. Chem.,* 1998, 41, 1745-1748; Barlaam, B.; Bird, T. G.; Lambert-van der Brempt, C.; et. al. *J. Med. Chem.,* 1999, 42, 4890-4902; Xue, C.-B.; Voss, M. E.; Nelson, D. J.; et. al. *J. Med. Chem.,* 2001, 44, 2636-2660; Kottirsch, G; et al. *J. Med. Chem.* 2002, 45, 2289-2293; Rabinowitz, M. H.; et al. *J. Med. Chem.* 2001, 44, 4252-4267; Beck, G.; et al. *J. Pharmacol. Exp. Ther.* 2002, 302, 390-396; WIPO international publications WO0032570, WO0035885, WO9918074, WO0059285] which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [*Scrip,* 1998, 2349, 20]. A lactam hydroxamic acid TACE inhibitor that is selective over many MMPs has been reported [Duan, J. J.-W.; et al. *J. Med. Chem.* 2002, 45, 4954-4957.]. Long-acting, selective, orally bioavailable non-peptide inhibitors of TACE would thus be highly desirable for the treatment of the disease states discussed above.

Matrix metalloproteinases (MMPs) are a group of enzymes that have been implicated in the pathological destruction of connective tissue and basement membranes. These zinc-containing endopeptidases consist of several subsets of enzymes including collagenases, stromelysins and gelatinases. Of these classes, the gelatinases have been shown to be the MMPs most intimately involved with the growth and spread of tumors. It is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology. Furthermore, there is evidence to suggest that gelatinase is involved in plaque rupture associated with atherosclerosis. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, scirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection. For recent reviews, see: Michaelides, M. R.; Curtin, M. L. *Curr. Pharm. Design* 1999, 5, 787-819 and Skiles, J. W.; Gonnella, N. C.; Jeng, A. Y. *Curr. Med. Chem.* 2001, 8, 425-474.

Examples of sulfonamide hydroxamic acid MMP/TACE inhibitors in which a 2-carbon chain separates the hydroxamic acid and the sulfonamide nitrogen, as shown below, are disclosed in WIPO international publications WO9816503, WO9816506, WO9816514 and WO9816520 and U.S. Pat. Nos. 5,929,097, 5,962,481, 5,977,408 6,162,814, 6,162821, 6,197,795, and 6,228,869. These compounds are further detailed by Levin, et al. in *Bioorg. Med. Chem. Lett.* 2001, 11, 235-238; *Bioorg. Med. Chem. Lett.* 2001, 11, 239-242; *Bioorg. Med. Chem. Lett.* 2001, 11, 2189-2192; *Bioorg. Med. Chem. Lett.* 2001, 11, 2975-2978.

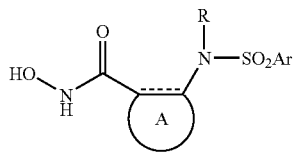

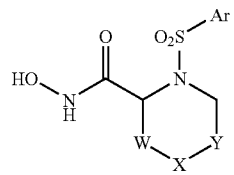

Examples of sulfonamide hydroxamic acid MMP/TACE inhibitors bearing an acetylenic substituent, are disclosed in WIPO international publications WO9839315, WO0044713, WO0044749, WO0044740, WO0044730, WO0044711, WO0044716, WO0044710, WO0044709, WO0044723, U.S. Pat. Nos. 6,200,996, 6,326,516, 6,277,885, 6,228,869, 6,225, 311, 6,313,123, Chen et al. in *Bioorg. Med. Chem. Lett.* 2002, 12, 1195-1198 and Levin, et al. in *Bioorg. Med. Chem. Lett.* 2002, 12, 1199-1202.

U.S. Pat. Nos. 5,455,258, 5,506,242, 5,552,419, 5,770, 624, 5,804,593 and 5,817,822 as well as European patent application EP606,046-A-1 and WIPO international publications WO9600214 and WO9722587 disclose non-peptide inhibitors of matrix metalloproteinases and/or TACE of which the aryl sulfonamide hydroxamic acid shown below, in which 1 carbon separates the hydroxamic acid and the sulfonamide nitrogen, is representative. Additional publications disclosing sulfonamide based MMP/TACE inhibitors which are variants of the sulfonamide-hydroxamate shown below, or the analogous sulfonamide-carboxylates, are European patent applications EP-757037-A1 and EP-757984-A1 and WIPO international publications WO9535275, WO9535276, WO9627583, WO9719068, WO9727174, WO9745402, WO9807697, and WO9831664, WO9833768, WO9839313, WO9839329, WO9842659, WO9843963, WO0110827, WO0127084. The discovery of this type of MMP/TACE inhibitor is further detailed by MacPherson, et. al. in *J. Med. Chem.*, (1997), 40, 2525-2532, Tamura, et al. in *J. Med. Chem.* (1998), 41, 640-649, Letavic, M. A.; et al. in *Bioorg. Med. Chem. Lett.* 2002, 12, 1387-1390, and Holms, J. et al. in *Bioorg. Med. Chem. Lett.* 2001, 11, 2907-2910.

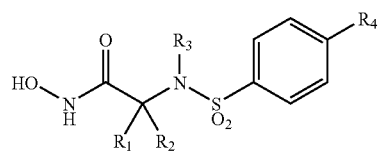

Publications disclosing α-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, WO0009492, Levin, et. al. *Bioorg. & Med. Chem. Letters* 1998, 8, 2657-2662 and Pikul, et. al. *J. Med. Chem.* 1998, 41, 3568-3571.

The patent applications DE19,542,189-A1, WO9718194, and EP803505 disclose additional examples of cyclic sulfonamides as MMP and/or TACE inhibitors. In this case the sulfonamide-containing ring is fused to an aromatic or heteroaromatic ring.

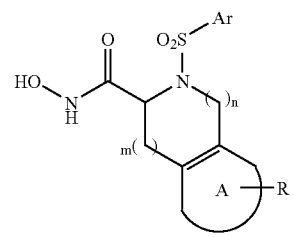

Analogous to the sulfonamides are the phosphinic acid amide hydroxamic acid MMP/TACE inhibitors, exemplified by the structure below, which have been disclosed in WIPO international publication WO9808853.

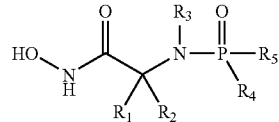

Sulfonamide MMP/TACE inhibitors in which a thiol is the zinc chelating group, as shown below, have been disclosed in WIPO international application 9803166 and U.S. Pat. No. 6,313,123.

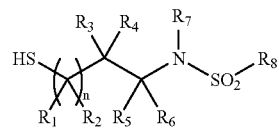

It is an object of this invention to disclose aryl sulfonate hydroxamic acid TACE inhibitors and MMP inhibitors in which the sulfonyl aryl group is para-substituted with a substituted butynyl moiety or a propargylic ether, amine or sulfide. These compounds inhibit the activity of TACE in vitro, and provide selectivity over MMP-1 and MMP-13. These compounds may therefore be used in the treatment of diseases mediated by TNF.

BRIEF SUMMARY OF THE INVENTION

The TACE inhibiting and MMP inhibiting aryl sulfonate hydroxamic acids of the present invention are represented by formula B:

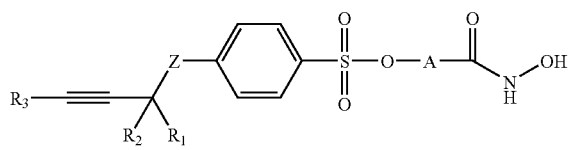

wherein:
R₁ and R₂ are each, independently, hydrogen, alkyl of 1-6 carbon atoms, —CN, or —CCH;
R₃ is hydrogen, alkyl of 1-6 carbon atoms, alkenyl of 2-6 carbon atoms, alkynyl of 2-6 carbon atoms, cycloalkyl of 3-6 carbon atoms, aryl of 6-12 carbon atoms, 5 to 10 membered heteroaryl having from 1 to 3 heteoatoms selected from N, NR₄, O or S, or 5 to 9 membered heterocycloalkyl having 1 or 2 heteroatoms selected from N, NR₄, O or S;
R₄ is hydrogen, aryl of 6-12 carbon atoms, alkyl of 1-6 carbon atoms, or cycloalkyl of 3-6 carbon atoms;
A is aryl of 6-12 carbon atoms, or phenyl fused to a 5 to 7 membered saturated or unsaturated cycloalkyl ring, a 5 to 9 membered saturated or unsaturated heterocycloalkyl ring having 1 or 2 heteroatoms selected from N, NR₄, O or S, or a heteroaryl ring having 5-10 members and from 1-3 heteroatoms selected from N, NR₄, O or S; wherein the C(=O)NHOH moiety and the —SO₃-moiety are bonded to adjacent carbons of A;
Z is O, NH, CH₂ or S;

or a pharmaceutically acceptable salt thereof.

Preferred compounds of the invention include compounds of formula B in which A is a phenyl or naphthyl or a pharmaceutically acceptable salt thereof.

Preferred compounds of the invention include compounds of formula B in which A is a phenyl or naphthyl wherein:
    Z is oxygen or a pharmaceutically acceptable salt thereof.

More preferred compounds of this invention include compounds of formula B in which A is a phenyl or naphthyl wherein:
    Z is oxygen;
    and R₁ and R₂ are hydrogen or a pharmaceutically acceptable salt thereof.

More preferred compounds of the invention include compounds of structure B in which A is a phenyl or naphthyl wherein:
    Z is oxygen;
    R₁ and R₂ are hydrogen;
    and R₃ is —CH₂OH or methyl or a pharmaceutically acceptable salt thereof.

Most preferred compounds of the present invention include:
2-[(hydroxyamino)carbonyl]-6-methylphenyl 4-(2-butynyloxy)benzenesulfonate;
2-[(hydroxyamino)carbonyl]-6-methoxyphenyl 4-(2-butynyloxy)benzenesulfonate;
2-[(hydroxyamino)carbonyl]-4,6-diisopropylphenyl 4-(2-butynyloxy)benzenesulfonate;
2-[(hydroxyamino)carbonyl]-4-methylphenyl 4-(2-butynyloxy)benzenesulfonate; and
3-[(hydroxyamino)carbonyl]-2-naphthyl 4-(2-butynyloxy)benzenesulfonate and pharmaceutical salts thereof.

Heteroaryl, as used herein is a 5-10 membered mono- or bicyclic aromatic ring having from 1-3 heteroatoms selected from N, NR₄, S and O. Heteroaryl is preferably

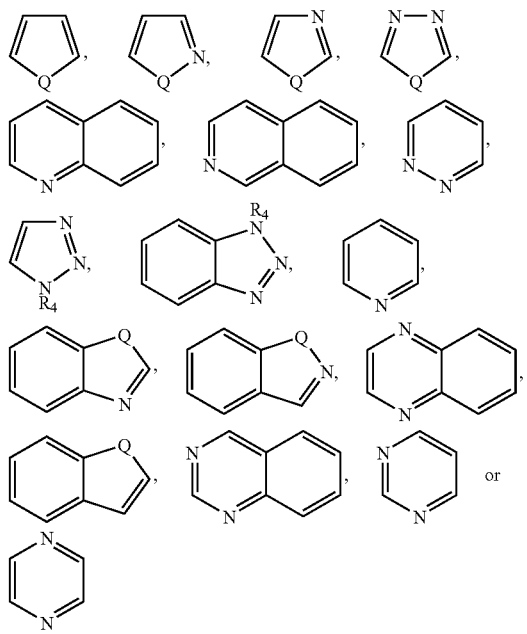

wherein Q is NR₄, O or S and R₄ is hydrogen, aryl of 6-12 carbon atoms, alkyl of 1-6 carbon atoms, or cycloalkyl of 3-6 carbon atoms. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. Heteroaryl groups of the present invention may optionally be independently mono- or di-substituted with groups selected from halogen, alkyl of 1-6 carbon atoms, alkenyl of 2-6 carbon atoms, alkynyl of 2-6 carbon atoms, cycloalkyl of 3-6 carbon atoms, —OR₅, —CN, —COR₅, perfluoroalkyl of 1-4 carbon atoms, —O-perfluoroalkyl of 1-4 carbon atoms, —CONR₅R₆, —S(O)ₙR₅ —OPO(OR₅)OR₆, —PO(OR₅)R₆, —OC(O)NR₅R₆, —C(O)NR₅R₆, —COOR₅, —SO₃H, —NR₅R₆, —N[(CH₂)₂]₂NR₅, —NR₅COR₆, —NR₅COOR₆, —SO₂NR₅R₆, —NO₂, —N(R₅)SO₂R₆, —NR₅CONR₅R₆, —NR₅C(=NR₆)NR₅R₆, —NR₅C(=NR₆)N(SO₂)R₅R₆, NR₅C(=NR)N(C=O)R₅R₆, NR₅C(=NR₆)N(SO₂R₅)R₆, NR₅C(=NR₆)N(COR₅)R₆, —SO₂NHCOR₇, —CONHSO₂R₇, -tetrazol-5-yl, —SO₂NHCN, —SO₂NHCONR₅R₆, aryl of 6-12 carbon atoms, heteroaryl and heterocycloalkyl;

R₅ and R₆ are each, independently, hydrogen, alkyl of 1-6 carbon atoms, cycloalkyl of 3-6 carbon atoms, aryl of 6-12 carbon atoms, heteroaryl or heterocycloalkyl; or when taken together in —NR₅R₆ form a pyrrolidine, piperidine, morpholine, thiomorpholine, oxazolidine, thiazolidine, pyrazolidine, piperazine, or azetidine ring;

R₇ is alkyl of 1-6 carbon atoms, alkenyl of 2-6 carbon atoms, alkynyl of 2-6 carbon atoms, cycloalkyl of 3-6 carbon atoms, perfluoroalkyl of 1-4 carbon atoms, aryl of 6-12 carbon atoms, heteroaryl or heterocycloalkyl; and n is 0 to 2.

Heterocycloalkyl as used herein refers to a 5 to 10 membered saturated or unsaturated mono or bi-cyclic ring having 1 or 2 heteroatoms selected from N, $NR_4$, S and O. Heterocycloalkyl rings of the present invention are preferably selected from;

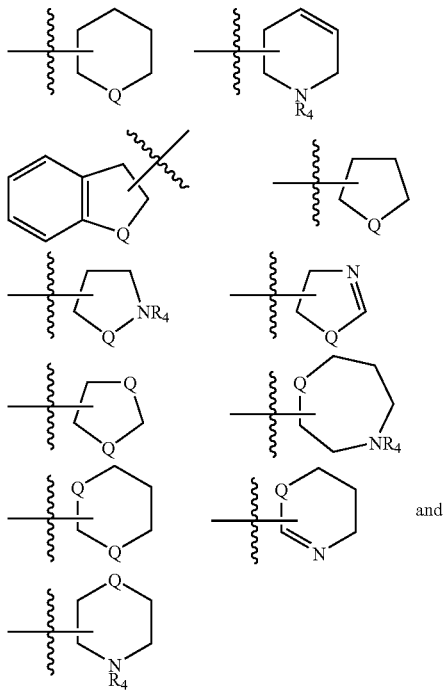

wherein Q is independently $NR_4$, O or S and $R_4$ is hydrogen, aryl of 6-12 carbon atoms, alkyl of 1-6 carbon atoms, or cycloalkyl of 3-6 carbon atoms. Preferred heterocycloalkyl rings include piperidine, piperazine, morpholine, tetrahydropyran, tetrahydrofuran or pyrrolidine. Heterocycloalkyl groups of the present invention may optionally be independently mono- or di-substituted with groups selected from halogen, alkyl of 1-6 carbon atoms, alkenyl of 2-6 carbon atoms, alkynyl of 2-6 carbon atoms, cycloalkyl of 3-6 carbon atoms, —$OR_5$, —CN, —$COR_5$, perfluoroalkyl of 1-4 carbon atoms, —O-perfluoroalkyl of 1-4 carbon atoms, —$CONR_5R_6$, —$S(O)_nR_5$ —$OPO(OR_5)OR_6$, —$PO(OR_5)R_6$, —$OC(O)NR_5R_6$, —$C(O)NR_5OR_6$, —$COOR_5$, —$SO_3H$, —$NR_5R_6$, —$N[(CH_2)_2]_2NR_5$, —$NR_5COR_6$, —$NR_5COOR_6$, —$SO_2NR_5R_6$, —$NO_2$, —$N(R_5)SO_2R_6$, —$NR_5CONR_5R_6$, —$NR_5C(=NR_6)NR_5R_6$, —$NR_5C(=NR_6)N(SO_2)R_5R_6$, $NR_5C(=NR_6)N(C=O)R_5R_6$, $NR_5C(=NR_6)N(SO_2R_5)R_6$, $NR_5C(=NR_6)N(COR_5)R_6$, —$SO_2NHCOR_7$, —$CONHSO_2R_7$, -tetrazol-5-yl, —$SO_2NHCN$, —$SO_2NHCONR_5R_6$, aryl of 6-12 carbon atoms, heteroaryl and heterocycloalkyl;

$R_5$ and $R_6$ are each, independently, hydrogen, alkyl of 1-6 carbon atoms, cycloalkyl of 3-6 carbon atoms, aryl of 6-12 carbon atoms, heteroaryl or heterocycloalkyl; or when taken together in —$NR_5R_6$ form a pyrrolidine, piperidine, morpholine, thiomorpholine, oxazolidine, thiazolidine, pyrazolidine, piperazine, or azetidine ring;

$R_7$ is alkyl of 1-6 carbon atoms, alkenyl of 2-6 carbon atoms, alkynyl of 2-6 carbon atoms, cycloalkyl of 3-6 carbon atoms; perfluoroalkyl of 1-4 carbon atoms, aryl of 6-12 carbon atoms, heteroaryl or heterocycloalkyl; and n is 0 to 2.

Aryl, as used herein refers to an aromatic hydrocarbon moiety of 6-12 carbon atoms and in particular to phenyl or naphthyl which may optionally be independently mono-, di-substituted or di-substituted with groups independently selected from halogen, alkyl of 1-6 carbon atoms, alkenyl of 2-6 carbon atoms, alkynyl of 2-6 carbon atoms, cycloalkyl of 3-6 carbon atoms, —$OR_5$, —CN, —$COR_5$, perfluoroalkyl of 1-4 carbon atoms, —O-perfluoroalkyl of 1-4 carbon atoms, —$CONR_5R_6$, —$S(O)_nR_5$—$OPO(OR_5)OR_6$, —$PO(OR_5)R_6$, —$OC(O)NR_5R_6$, —$C(O)NR_5OR_6$, —$COOR_5$, —$SO_3H$, —$NR_5R_6$, —$N[(CH_2)_2]_2NR_5$, —$NR_5COR_6$, —$NR_5COOR_6$, —$SO_2NR_5R_6$, —$NO_2$, —$N(R_5)SO_2R_6$, —$NR_5CONR_5R_6$, —$NR_5C(=NR_6)NR_5R_6$, —$NR_5C(=NR_6)N(SO_2)R_5R_6$, $NR_5C(=NR_6)N(C=O)R_5R_6$, $NR_5C(=NR_6)N(SO_2R_5)R_6$, $NR_5C(=NR_6)N(COR_5)R_6$, —$SO_2NHCOR_7$, —$CONHSO_2R_7$, -tetrazol-5-yl, —$SO_2NHCN$, —$SO_2NHCONR5R_6$, aryl of 6-12 carbon atoms, heteroaryl and heterocycloalkyl;

$R_5$ and $R_6$ are each, independently, hydrogen, alkyl of 1-6 carbon atoms, cycloalkyl of 3-6 carbon atoms, aryl of 6-12 carbon atoms, heteroaryl or heterocycloalkyl; or when taken together in —$NR_5R_6$ form a pyrrolidine, piperidine, morpholine, thiomorpholine, oxazolidine, thiazolidine, pyrazolidine, piperazine, or azetidine ring;

$R_7$ is alkyl of 1-6 carbon atoms, alkenyl of 2-6 carbon atoms, alkynyl of 2-6 carbon atoms, cycloalkyl of 3-6 carbon atoms, perfluoroalkyl of 1-4 carbon atoms, aryl of 6-12 carbon atoms, heteroaryl or heterocycloalkyl; and n is 0 to 2.

As used herein, alkyl of 1 to 6 carbon atoms, alkenyl of 2 to 6 carbon atoms, alkynyl of 2 to 6 carbon atoms, and perfluoroalkyl of 1 to 6 carbon atoms include both straight chain as well as branched moieties. Alkyl, alkenyl, alkynyl, and cycloalkyl groups may be unsubstituted, where unsubstituted means (carbons bonded to hydrogen, or other carbons in the chain or ring) or may be mono- or poly-substituted with halogen, alkyl of 1-6 carbon atoms, alkenyl of 2-6 carbon atoms, alkynyl of 2-6 carbon atoms, cyclocalkyl of 3-6 carbon atoms, —$OR_5$, —CN, —$COR_5$, perfluoroalkyl of 1-4 carbon atoms, —O-perfluoroalkyl of 1-4 carbon atoms, —$CONR_5R_6$, —$S(O)_nR_5$—$OPO(OR_5)OR_6$, —$PO(OR_5)R_6$, —$OC(O)NR_5R_6$, —$C(O)NR_5OR_6$, —$COOR_5$, —$SO_3H$, —$NR_5R_6$, —$N[(CH_2)_2]_2NR_5$, —$NR_5COR_6$, —$NR_5COOR_6$, —$SO_2NR_5R_6$, —$NO_2$, —$N(R_5)SO_2R_6$, —$NR_5CONR_5R_6$, —$NR_5C(=NR_6)NR_5R_6$, —$NR_5C(=NR_6)N(SO_2)R_5R_6$, $NR_5C(=O)R_5R_6$, $NR_5C(=NR)N(SO_2R_5)R_6$, $NR_5C(=NR_6)N(COR_5)R_6$, —$SO_2NHCOR_7$, —$CONHSO_2R_7$, -tetrazol-5-yl, —$SO_2NHCN$, —$SO_2NHCONR_5R_6$, aryl of 6-12 carbon atoms, or heteroaryl.

Halogen means bromine, chlorine, fluorine, and iodine.

The term alkyl, alone or in combination, means a straight-chain or branched-chain alkyl radical containing from 1 to 6 carbon atoms optionally substituted. Examples of such radicals include methyl, ethyl, n-propyl, isopropyl, n-butyl, isobutyl, sec-butyl, tert-butyl, and pentyl, and the like.

The term alkenyl, alone or in combination, means a straight-chain or branched-chain hydrocarbon radial having one or more double bonds and containing from 2 to 6 carbon atoms optionally substituted. Examples of suitable alkenyl radicals include ethenyl (vinyl), 2-propenyl, 3-propenyl, 1,4-pentadienyl, 1,4-butadienyl, 1-butenyl, 2-butenyl, and 3-butenyl and the like.

The term alkynyl, alone or in combination, means a straight-chain hydrocarbon radical having one or more triple bonds and containing from 2 to 6 carbon atoms optionally substituted. Examples of alkynyl radicals include ethynyl, 2-propynyl, 3-propynyl, decynyl, 1-butynyl, and 2-butynyl and the like.

The term perfluoroakyl means an alkyl group wherein each hydrogen has been replaced by a fluorine atom. Examples of perfluoroalkyl groups include trifluoromethyl, perfluorobutyl, and perfluoroisopropyl and the like.

Cycloalkyl refers to cyclic alkyl groups of 3-6 carbon atoms optionally substituted with halogen, alkyl of 1-6 carbon atoms, alkenyl of 2-6 carbon atoms, alkynyl of 2-6 carbon atoms, cyclocalkyl of 3-6 carbon atoms, $-OR_5$, $-CN$, $-COR_5$, perfluoroalkyl of 1-4 carbon atoms, $-O$-perfluoroalkyl of 1-4 carbon atoms, $-CONR_5R_6$, $-S(O)_nR_5$ $-OPO(OR_5)OR_6$, $-PO(OR_5)R_6$, $-OC(O)NR_5R_6$, $-C(O)NR_5OR_6$, $-COOR_5$, $-SO_3H$, $-NR_5R_6$, $-N[(CH_2)_2]_2NR_5$, $-NR_5COR_6$, $-NR_5COOR_6$, $-SO_2NR_5R_6$, $-NO_2$, $-N(R_5)SO_2R_6$, $-NR_5CONR_5R_6$, $-NR_5C(=NR_6)NR_5R_6$, $-NR_5C(=NR_6)N(SO_2)R_5R_6$, $NR_5C(=NR_6)N(C=O)R_5R_6$, $NR_5C(=NR_6)N(SO_2R_5)R_6$, $NR_5C(=NR_6)N(COR_5)R_6$, $-SO_2NHCOR_7$, $-CONHSO_2R_7$, -tetrazol-5-yl, $-SO_2NHCN$, $-SO_2NHCONR_5R_6$, aryl of 6-12 carbon atoms, heteroaryl or heterocycloalkyl;

$R_5$ and $R_6$ are each, independently, hydrogen, alkyl of 1-6 carbon atoms, cycloalkyl of 3-6 carbon atoms, aryl of 6-12 carbon atoms, heteroaryl or heterocycloalkyl; or when $R_5$ and $R_6$ are taken together in $-NR_5R_6$ form a pyrrolidine, piperidine, morpholine, thiomorpholine, oxazolidine, thiazolidine, pyrazolidine, piperazine, or azetidine ring;

$R_7$ is alkyl of 1-6 carbon atoms, alkenyl of 2-6 carbon atoms, alkynyl of 2-6 carbon atoms, cycloalkyl of 3-6 carbon atoms, perfluoroalkyl of 1-4 carbon atoms, aryl of 6-12 carbon atoms, heteroaryl or heterocycloalkyl; and n is 0 to 2.

Suitable substituents of aryl of 6-12 carbon atoms, heteroaryl, alkyl, alkenyl, alkynyl, cycloalkyl and include, but are not limited to halogen, alkyl of 1-6 carbon atoms, alkenyl of 2-6 carbon atoms, alkynyl of 2-6 carbon atoms, cyclocalkyl of 3-6 carbon atoms, $-OR_5$, $-CN$, $-COR_5$, perfluoroalkyl of 1-4 carbon atoms, $-O$-perfluoroalkyl of 1-4 carbon atoms, $-CONR_5R_6$, $-S(O)_nR_5$ $-OPO(OR_5)OR_6$, $-PO(OR_5)R_6$, $-OC(O)NR_5R_6$, $-C(O)NR_5OR_6$, $-COOR_5$, $-SO_3H$, $-NR_5R_6$, $-N[(CH_2)_2]_2NR_5$, $-NR_5COR_6$, $-NR_5COOR_6$, $-SO_2NR_5R_6$, $-NO_2$, $-N(R_5)SO_2R_6$, $-NR_5CONR_5R_6$, $-NR_5C(=NR_6)NR_5R_6$, $-NR_5C(=NR_6)N(SO_2)R_5R_6$, $-NR_5C(=NR_6)N(C=O)R_5R_6$, $NR_5C(=NR_6)N(SO_2R_5)R_6$, $-NR_5C(=NR_6)N(COR_5)R_6$, $-SO_2NHCOR_7$, $-CONHSO_2R_7$, -tetrazol-5-yl, $-SO_2NHCN$, $-SO_2NHCONR_5R_6$, aryl of 6-12 carbon atoms, heteroaryl or heterocycloalkyl;

$R_5$ and $R_6$ are each, independently, hydrogen, alkyl of 1-6 carbon atoms, cycloalkyl of 3-6 carbon atoms, aryl of 6-12 carbon atoms, heteroaryl or heterocycloalkyl; or when $R_5$ and $R_6$ are taken together in $-NR_5R_6$ form a pyrrolidine, piperidine, morpholine, thiomorpholine, oxazolidine, thiazolidine, pyrazolidine, piperazine, or azetidine ring;

$R_7$ is alkyl of 1-6 carbon atoms, alkenyl of 2-6 carbon atoms, alkynyl of 2-6 carbon atoms, cycloalkyl of 3-6 carbon atoms, perfluoroalkyl of 1-4 carbon atoms, aryl of 6-12 carbon atoms, heteroaryl or heterocycloalkyl; and n is 0 to 2.

Suitable substituents of heterocycloalkyl groups of the present invention include, but are not limited to alkyl of 1-6 carbon atoms, cycloalkyl of 3-6 carbon atoms, aryl of 6-12 carbon atoms, heteroaryl and heterocycloalkyl.

When a moiety contains more than substituent with the same designation each of those substituents may be the same or different.

Pharmaceutically acceptable salts are formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Pharmaceutically acceptable salts are also formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes TNF-α converting enzyme (TACE), MMP-1 and MMP-13 and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro or enhanced selectivity over MMP-1 and MMP-13 and are thus particularly useful in the treatment of diseases mediated by TNF.

In a second aspect, the invention relates to a method of inhibiting pathological changes mediated by TNF-α converting enzyme (TACE) in a mammal in need thereof which comprises administering to said mammal a therapeutically effective amount of a compound of the invention.

In a third aspect, the invention relates to a pharmaceutical composition comprising a compound of the invention and a pharmaceutically acceptable carrier.

In a fourth aspect, the invention relates to a method of inhibiting pathological changes mediated by matrix metalloproteinases in mammals which comprises administration to a mammal in need thereof a therapeutically effective amount of a matrix metalloproteinase inhibiting compound of the invention.

The invention compounds are prepared using conventional techniques known to those skilled in the art of organic synthesis. The starting materials used in preparing the compounds of the invention are known, made by known methods or are commercially available.

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts "Protective Groups in Organic Synthesis", 2$^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions.

When preparing or elaborating compounds of the invention containing aryl, heteroaryl or heterocyclic rings, those skilled in the art recognize that substituents on that ring may be prepared before, after or concomitant with construction of the ring. For clarity, substituents on such rings have been omitted from the schemes herein below.

Non-limiting processes to prepare compounds of the invention are described herein in Schemes 1-5.

by reaction with hydroxylamine to give hydroxamic acid 1, or with a protected hydroxylamine derivative to give protected hydroxamic acid 3. Protected hydroxamic acid 3, wherein $R_8$ is a t-butyl, benzyl, trialkylsilyl or other suitable masking group may then be deprotected by known methods to provide the hydroxamic acid 1.

Suitable peptide coupling reagents are selected from the group N,N'-dicyclohexylcarbodiimide plus 1-hydroxybenzotriazole, benzotriazol-1-yloxytris(dimethylamino)phosphonium hexafluorophosphate (BOP-reagent), N,N'bis[2-oxo-3-oxazolidinyl]phosphorodiamidic chloride (BOB Cl), diphenylphosphinyl chloride (DPP-Cl), diethoxyphosphoryl cyanide, 2-chloro-1-methylpyridinium iodide, phenyldichlorophosphate plus imidazole, 2-(1H-benzotriazole-1-yl)-1,1,3,3-tetramethyluronium tetrafluoroborate, 2-(1H-benzotriazole-1-yl)-1,1,3,3-tetramethyluronium hexafluorophosphate, bromo-tris-pyrrolidino-phosphonium hexafluorophosphate and benzotriazole-1-yl-oxy-tris-pyrrolidino-phosphonium hexafluorophosphate in the presence of N,N-diisopropylethylamine, or other organic base which includes but are not limited to: N,N-diisopropylethylamine, N-methylmorpholine, N-methylpyrrolidine, triethylamine, 4-dimethylaminopyridine, 2,6-di-tert-butyl-4-methylpyridine and pyridine.

Scheme 1:

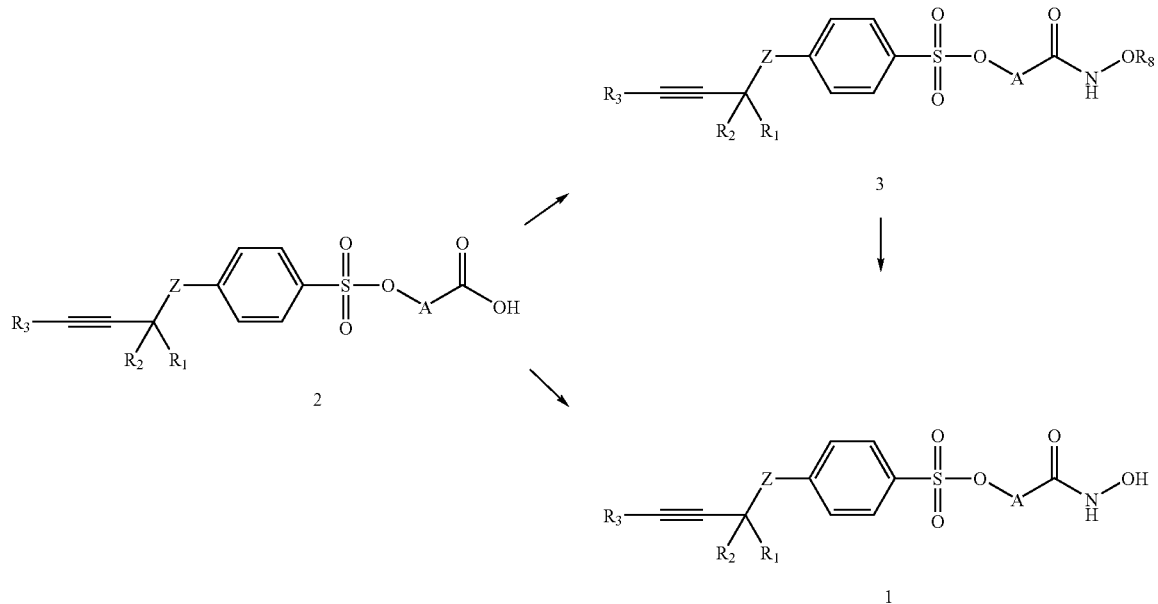

Those skilled in the art will recognize that the nature and order of the synthetic steps presented may be varied for the purpose of optimizing the formation of the compounds of the invention.

DETAILED DESCRIPTION OF THE INVENTION

The hydroxamic acid compounds of the invention, 1, are prepared according to Scheme 1 by converting a carboxylic acid, 2, into the corresponding acid chloride or anhydride, or by reaction with a suitable peptide coupling reagent, followed Carboxylic acids 2 may be prepared as shown in Scheme 2. Salicylic acid derivative 4, in which $R_9$ is hydrogen or a suitable carboxylic acid protecting group, may be sulfonylated to give ester 6 by reacting with alkyne 5, in which J is a suitable leaving group including leaving group which includes but not limited to chloro, bromo, p-toluenesulfonyl and methanesulfonyl. Conversion of ester 6 to the carboxylic acid 2 is performed by reaction with lithium iodide in ethyl acetate, or other method consistent with the choice of protecting group $R_9$, the presence of a carbon-carbon triple bond, and a sulfonate ester. $R_9$ is defined as alkyl of 1-6 carbon atoms optionally substituted.

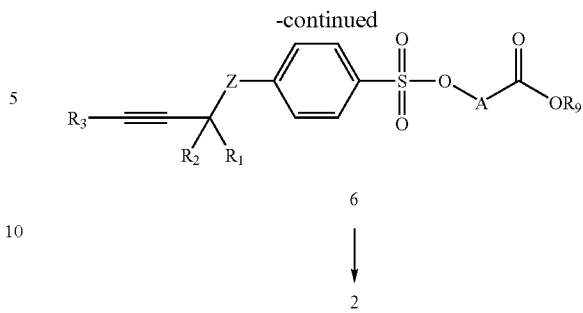

6

↓

2

The acetylenic side chain may also be appended after sulfonylation of the salicylic acid derivative, as shown in Scheme 3. Thus, the salicylic acid derivatives 4 can be sulfonylated with compounds 7, where $ZR_{10}$ is hydroxy or protected hydroxy, thiol or amine where the $R_{10}$ protecting group moieties may be found in T. W. Greene, P. G. M. Wuts "Protective Groups in Organic Synthesis", $2^{nd}$ Edition, 1991, Wiley & Sons, New York, to give ester 8. Removal of the $R_{10}$ masking group to give sulfonyl 9 and subsequent alkylation of the resulting phenol, thiol or amine with alkyne 10 provides ester 6. In the case where $ZR_{10}$ is equal to OH, no deprotection step is required to give sulfonyl 9.

Scheme 2:

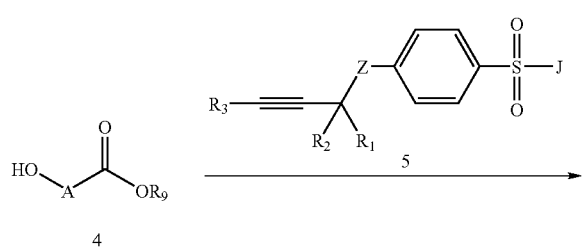

Scheme 3:

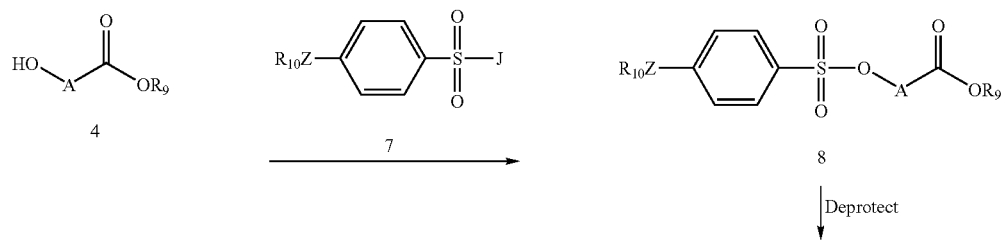

| Deprotect
↓

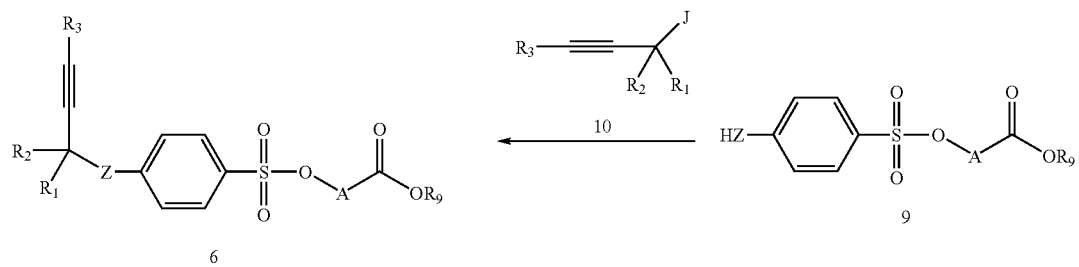

The propargylic amine analogs of 6 can be synthesized as shown in Scheme 4 starting from the salicylic acid derivatives 4. Sulfonylation with para-nitro aryl compound 11, for example 4-nitrobenzenesulfonyl chloride provides nitro 12. Reduction of the nitro moiety with hydrogen and palladium on carbon, tin chloride or other known method to give aniline 13 and subsequent alkylation with alkyne 10 then provides ester 6 (Z═NH). Aniline 13 may be derivatized with a suitable nitrogen protecting group, such as t-butoxycarbonyl, to give substituted aniline 14 prior to alkylation with alkyne 10 followed by subsequent deprotection after the alkylation step.

$R_{11}COR_{12}$ or a halide, sulfonate or triflate of the formula $R_{11}CH_2J$ provides alcohol 15 and 16. Reaction of ester 6 with formaldehyde and an amine provides the Mannich addition product 17. $R_{11}$ is alkyl of 1-6 carbon atoms, cycloalkyl of 3-6 carbon atoms, aryl of 6-12 carbon atoms, 5 to 10 membered heteroaryl having from 1 to 3 heteroatoms selected from N, $NR_4$, O or S, or 5 to 9 membered heterocycloalkyl having 1 or 2 heteroatoms selected from N, $NR_4$, O or $R_{12}$ is hydrogen, alkyl of 1-6 carbon atoms, cycloalkyl of 3-6 carbon atoms, aryl of 6-12 carbon atoms, 5 to 10 membered heteroaryl having from 1 to 3 heteroatoms selected from N, $NR_4$, O or S, Scheme 4:

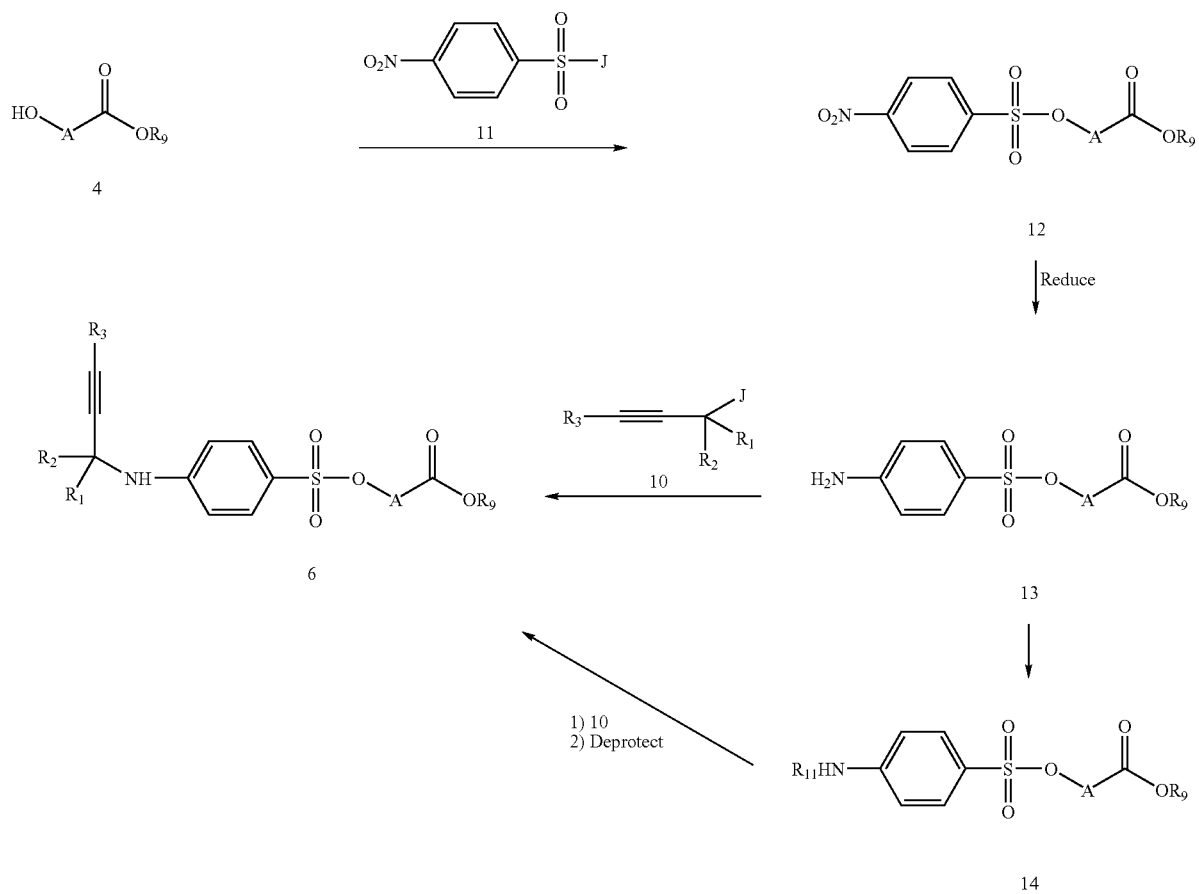

or 5 to 9 membered heterocycloalkyl having 1 or 2 heteroatoms selected from N, $NR_4$, O or S.

Cyanogen bromide addition to Mannich addition product 17 gives the propargylic bromide 18 which may be displaced with a variety of nucleophiles in the presence of a base to give, for example, ethers, thioethers and amines 19 where ZR is —$OR_5$, —$NR_5R_6$ or —$SR_5$. Suitable base includes alkali metal carbonates such as potassium carbonate and sodium carbonate, tertiary amines which include triethylamine and the like and alkoxide bases which include sodium ethoxide and the like. Palladium catalyzed coupling reactions of ester 6 provide the aryl of 6-12 carbon atoms or heteroaryl acetylenes 20. It is recognized by those skilled in the art of organic synthesis that the successful use of these methods is dependent upon the compatibility of substituents on other parts of the molecule. Protecting groups and/or changes in the order of steps described herein may be required.

Compounds of the invention can also be prepared by modifying substituents on the acetylenic side chain at any stage after sulfonylation of the starting salicylic acid derivatives 4. Functional groups such as but not limited to halogen, hydroxy, amino, aldehyde, ester, or ketone may be manipulated by standard methods to form the moieties defined by $R_1$-$R_8$ of hydroxamic acid compounds 1. It is recognized by those skilled in the art of organic synthesis that the successful use of these methods is dependent upon the compatibility of substituents on other parts of the molecule. Protecting groups and/or changes in the order of steps described herein may be required.

Some of the methods available for the derivatization of compounds of ester 6 ($R_3$═H) are shown in Scheme 5. Metallation of the terminal acetylene of ester 6 ($R_3$═H) followed by addition of an aldehyde or ketone of the formula Scheme 5:
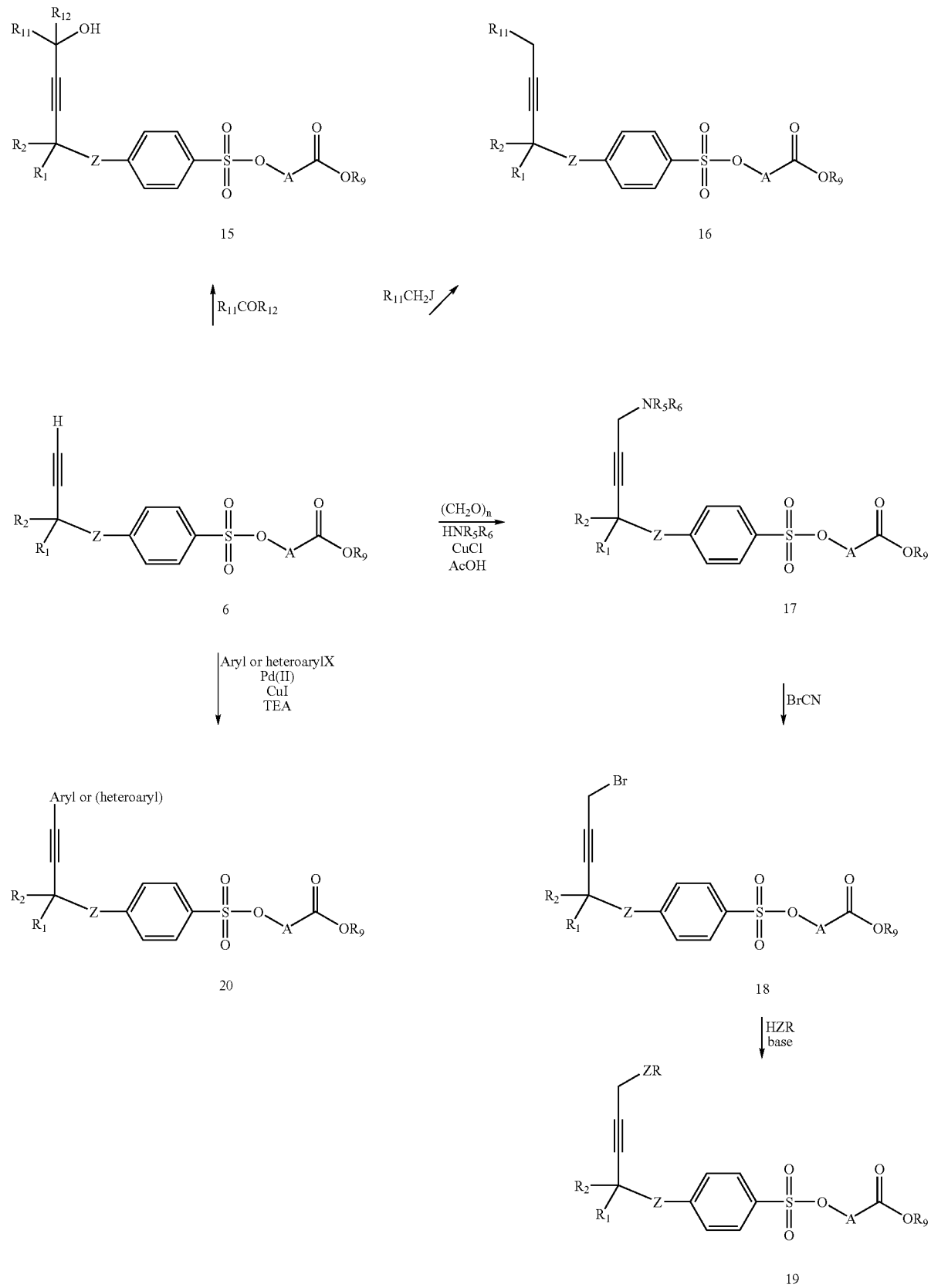

The following specific examples illustrate the preparation of representative compounds of this invention. The starting materials, intermediates, and reagents are either commercially available or can be readily prepared following standard literature procedures by one skilled in the art of organic synthesis.

EXAMPLE 1

2-[(Hydroxyamino)carbonyl]-6-methylphenyl 4-(2-butynyloxy)benzenesulfonate

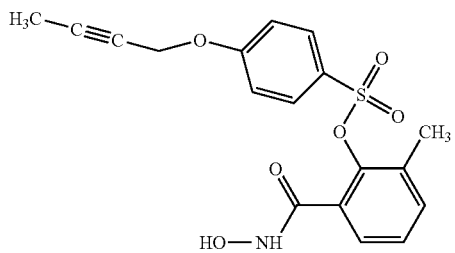

Step 1

To a solution of 0.50 g (3.012 mmol) of methyl 2-hydroxy-3-methyl-benzoate in 20 mL of tetrahydrofuran (THF) is added 0.133 g (3.313 mmol) of a 60% oil dispersion of sodium hydride. The reaction mixture is stirred for 1 h at room temperature and then 0.739 g (3.012 mmol) of 4-but-2-ynyloxy benzenesulfonyl chloride is added. The resulting mixture is stirred at room temperature for 15 h and then quenched with saturated ammonium chloride solution. The resulting mixture is extracted with ether and the combined organics are then washed with water and brine. The organic layer is then dried over MgSO$_4$, filtered and concentrated in vacuo. The residue is chromatographed on silica gel eluting with ethyl acetate/hexanes (1:3) to provide 0.93 g (83%) of methyl 2-({[4-(2-butynyloxy)phenyl]sulfonyl}oxy)-3-methylbenzoate as a white solid. Electrospray Mass Spec: 374.8 (M+H)$^+$ Step 2

To a solution of 0.200 g (0.535 mmol) of the product of Step 1 in 12 mL of ethyl acetate is added 0.716 g (5.35 mmol) of lithium iodide and the resulting mixture is heated to reflux for 24 h. An additional 0.716 g (5.35 mmol) of lithium iodide is then added and the reaction mixture is heated to reflux for an additional 6 h. The reaction is then let cool to room temperature and washed with 5% HCl solution, sodium thiosulfate solution, and brine. The organics are then dried over MgSO$_4$, filtered and concentrated in vacuo to afford 0.123 g (64%) of 2-({[4-(2-butynyloxy)phenyl]sulfonyl}oxy)-3-methylbenzoic acid as a white solid pure enough for use in the next step. Electrospray Mass Spec: 358.8 (M–H)$^-$ Step 3

To a solution of 0.125 g (0.347 mmol) of the product of Step 2 in 4.4 mL of N,N-dimethylformamide (DMF) is added 0.056 g (0.417 mmol) of 1-hydroxybenzotriazole hydrate (HOBT) followed by 0.089 g (0.462 mmol) of 1-(3-dimethylaminopropyl)-3-ethylcarbodiimide hydrochloride (EDC). The resulting mixture is stirred for 1 h at room temperature and then 0.095 mL of a 50% aqueous solution of hydroxylamine is added and the reaction mixture is stirred overnight. The reaction mixture is then diluted with ethyl acetate and washed with water and brine. The organics are dried over sodium sulfate, filtered and concentrated in vacuo. The residue is chromatographed on silica gel eluting with a gradient of ethyl acetate-hexanes (1:1 to 2:1) to provide 0.065 g (50%) of 2-[(hydroxyamino)carbonyl]-6-methylphenyl 4-(2-butynyloxy)benzenesulfonate as a white solid. Electrospray Mass Spec: 376.0 (M+H)$^+$

EXAMPLE 2

2-[(Hydroxyamino)carbonyl]-6-methoxyphenyl 4-(2-butynyloxy)benzenesulfonate

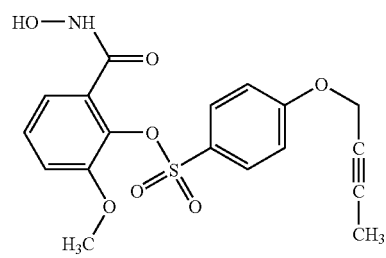

According to the procedure of Example 1, methyl 3-methoxy salicylate provided 2-[(hydroxyamino)carbonyl]-6-methoxyphenyl 4-(2-butynyloxy)benzenesulfonate as a white solid. Electrospray Mass Spec: 390.2 (M–H)$^-$

EXAMPLE 3

2-[(Hydroxyamino)carbonyl]-4-methylphenyl 4-(2-butynyloxy)benzenesulfonate

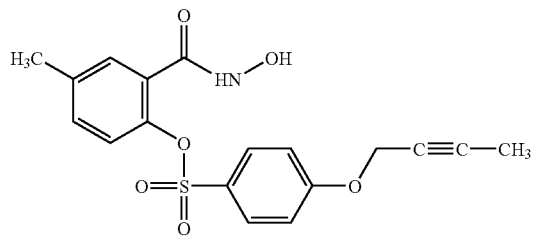

According to the procedure of Example 1, methyl 5-methyl salicylate provided 2-[(hydroxyamino)carbonyl]-4-methylphenyl 4-(2-butynyloxy)benzenesulfonate as a white solid. Electrospray Mass Spec: 374.2 (M–H)$^-$

EXAMPLE 4

2-[(Hydroxyamino)carbonyl]-4,6-diisopropylphenyl 4-(2-butynyloxy)benzenesulfonate

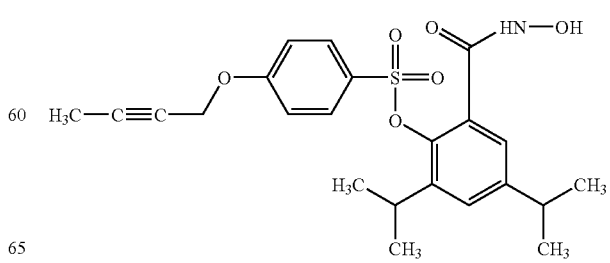

According to the procedure of Example 1, methyl 3,5-diisopropyl salicylate provided 2-[(hydroxyamino)carbonyl]-4,6-diisopropylphenyl 4-(2-butynyloxy)benzenesulfonate as a white solid. Electrospray Mass Spec: 444.2 (M–H)⁻

EXAMPLE 5

3-[(Hydroxyamino)carbonyl]-2-naphthyl 4-(2-butynyloxy)benzenesulfonate

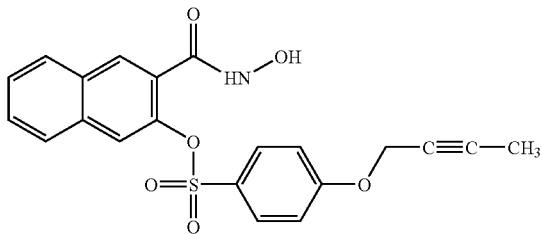

According to the procedure of Example 1, methyl 3-hydroxy-2-naphthoate provided 3-[(hydroxyamino)carbonyl]-2-naphthyl 4-(2-butynyloxy)benzenesulfonate as a white solid. Electrospray Mass Spec: 410.1 (M–H)⁻

Pharmacology

Standard Pharmacological Test Procedures

Representative compounds of this invention are evaluated as inhibitors of the enzymes MMP-1 and MMP-13 and TNF-α converting enzyme (TACE). The standard pharmacological test procedures used, and results obtained which establish this biological profile are shown below.

Test Procedures for Measuring MMP-1 and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1 or MMP-13 (collagenases) which results in the release of a substrate product that reacts colorimetrically with DTNB (5,5'-dithiobis(2-nitrobenzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1 or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generated using multiple doses of drug and $IC_{50}$ values with 95% Cl are estimated using linear regression.

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generate using multiple doses of drug and $IC_{50}$ values with 95% Cl are estimated using linear regression.

Human Monocytic THP-1 Cell Differentiation Assay for Soluble Proteins (THP-1 Soluble Protein Assay)

Mitogenic stimulation of THP-1 cells cause differentiation into macrophage like cells with concomitant secretion of tumor necrosis factor (TNF-a) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-α and possibly TNF-R p75/80 and TNF-R p55/60, but not IL-8, is mediated by an enzyme called TNF-a converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which are obtained from the peripheral blood of a one year old male with acute monocytic leukemia. They can be grown in culture and differentiated into macrophage like cells by stimulation with mitogens.

For the assay, THP-1 cells are seeded from an ATCC stock which is previously grown and frozen back at 5×106/ml/vial. One vial is seeded into a T25-flask with 16 mls of RPMI-1640 with glutamax (Gibco) media containing 10% fetal bovine serum, 100 units/ml penicillin, 100 μg/ml streptomycin, and 5×10⁻⁵ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105/ml.

To perform an assay, the THP-1 cells are co-incubated in a 24 well plate with 50 ml/well of a 24 mg/ml stock of Lipopolysacharide (LPS) (Calbiochem Lot# B13189) at 37° C. in 5% $CO_2$ at a concentration of $1.091 \times 10^6$ cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO is limited to 0.1% final concentration. Positive control wells are included in the experiment which had mitogen added but no drug. Vehicle control wells are included as well, which are identical to the positive control wells, except that DMSO is added to give a final concentration of 0.083%. Negative control wells are included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-a ELISA. Following 24 hours of incubation, 700 ml/well of TCS is removed and used for analysis in TNF-R p75/80, TNF-R p55/60 and IL-8 ELISAs.

In addition, at the 24 hours timepoint, and the cells for each treatment group are collected by resuspension in 500 μl/well of THP-1 media and transferred into a FACS tube. Two ml/tube of a 0.5 mg/ml stock of propidium iodide (PI) (Boerhinger Mannheim cat. #1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups are compared to the viability value calculated for the vehicle treated mitogen stimulated group ("vehicle positive control") to determine the "percent change from control". This "percent change from control" value is an indicator of drug toxicity.

The quantity of soluble TNF-a, TNF-R p75/80 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration. Percent change in each soluble protein evaluated from the "vehicle positive control" is calculated for each compound concentration with the following formula:

$$\% \text{ Change} = \frac{pg/\text{ml (compound)} - pg/\text{ml (veh pos control)}}{pg/\text{ml (veh pos control)} - pg/\text{ml (veh neg control)}} \times 100$$

For the soluble protein (TNF-a, p75/80, p55/60, IL-8) studies under stimulated conditions, the mean pg/ml of duplicate wells are determined and the results expressed as percent change from "vehicle positive control". For the soluble protein (p75/80 and p55/60 receptors) studies under non-stimulated conditions, the mean pg/ml of duplicate wells are determined and the results expressed as percent change from "vehicle positive control" utilizing the following formula:

$$\% \text{ Change} = \frac{pg/\text{ml (compound } neg \text{ control)} - pg/\text{ml (}veg\ neg\text{ control)}}{pg/\text{ml (}veh\ neg\text{ control)}} \times 100$$

IC50 values for each compound are calculated by non-linear regression analysis using customized software utilizing the JUMP statistical package.

For the cell viability studies, the viabilities (PI exclusion) of pooled duplicate wells are determined and the results expressed as % change from "vehicle positive control". The viability values calculated for the compound treated groups are compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (}veh\ pos\text{ control)}} - 1 \times 100$$

REFERENCES

Bjornberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203-211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-1 cells in vitro. Cellular Immun. 138:1-10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:171-176, 1980.

Results of the above in-vitro and matrix metalloproteinase inhibition, TACE inhibition and THP standard pharmacological test procedures are given in Table I below.

TABLE I

Inhibition in MMP, TACE and THP assays:
Sulfonate Ester TACE Inhibitors

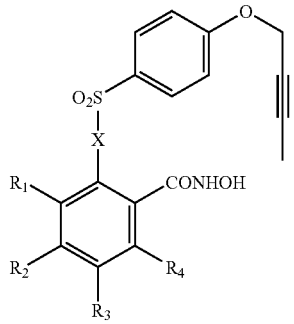

| Example | X | $R_1$ | $R_2$ | $R_3$ | $R_4$ | MMP-1[a] | MMP-13[a] | TACE[a] | THP[b] |
|---|---|---|---|---|---|---|---|---|---|
| 1 | O | Me | H | H | H | 11%(10) | 38%(10) | 19 | 11 |
| 2 | O | OMe | H | H | H | 7%(10) | 56%(10) | 13 | 1 |
| 3 | O | H | H | Me | H | 11%(10) | 27%(10) | 31 | 0 |
| 4 | O | iPr | H | iPr | H | 3%(10) | 45%(10) | 361 | 6 |
| 5 | O | H | —CH═CH—CH═CH— | | H | 16%(10) | 64%(10) | 67 | 0 |

[a]$IC_{50}$ (nM) or % Inhib (μM)
[b]% Inhibition @ 1 μM

Based on the results obtained in the standard pharmacological test procedures described above, the compounds of this invention are shown to be inhibitors of the enzyme TNF-a converting enzyme (TACE) and are therefore useful as a method of treatment of disorders such as rheumatoid arthritis, graft rejection, cachexia, inflammation, fever, insulin resistance, septic shock, congestive heart failure, inflammatory disease of the central nervous system, inflammatory bowel disease or HIV infection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A method of treating a disease or disorder mediated by TNF-α converting enzyme (TACE) in a mammal in need thereof which comprises administering to said mammal a therapeutically effective amount of a compound having the formula B:

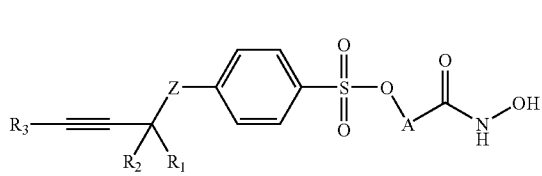

wherein:
$R_1$ and $R_2$ are each, independently, hydrogen, alkyl of 1-6 carbon atoms, —CN, or —C≡CH;
$R_3$ is hydrogen, alkyl of 1-6 carbon atoms, alkenyl of 2-6 carbon atoms, alkynyl of 2-6 carbon atoms, cycloalkyl of 3-6 carbon atoms, aryl of 6-12 carbon atoms, 5 to 10 membered heteroaryl having from 1 to 3 heteroatoms selected from N, $NR_4$, O and S, or 5 to 9 membered heterocycloalkyl having 1 or 2 heteroatoms selected from N, $NR_4$, O and S;
$R_4$ is hydrogen, aryl of 6-12 carbon atoms, alkyl of 1-6 carbon atoms, or cycloalkyl of 3-6 carbon atoms;
A is aryl of 6-12 carbon atoms, or phenyl fused to a 5 to 7 membered saturated or unsaturated cycloalkyl ring, a 5 to 9 membered saturated or unsaturated heterocycloalkyl ring having 1 or 2 heteroatoms selected from N, $NR_4$, O and S, or a heteroaryl ring having 5-10 members and from 1-3 heteroatoms selected from N, $NR_4$, O and S; wherein the C(=O)NHOH moiety and the —$SO_3$— moiety are bonded to adjacent carbons of A;
Z is O, NH, $CH_2$ or S;
wherein said heteroaryl is optionally independently mono- or di-substituted;
wherein said aryl is optionally independently mono-, di-substituted or tri-substituted;
wherein said alkyl, alkenyl, alkynyl, and cycloalkyl groups may be unsubstituted or may be independently mono- or poly-substituted;
wherein said heterocycloalkyl groups may be optionally independently mono- or di-substituted;
wherein the substituents of the heteroaryl, aryl, alkyl, alkenyl, alkynyl, cycloalkyl and heterocycloalkyl are selected from halogen, alkyl of 1-6 carbon atoms, alkenyl of 2-6 carbon atoms, alkynyl of 2-6 carbon atoms, cyclocalkyl of 3-6 carbon atoms, —$OR_5$, —CN, —$COR_5$, perfluoroalkyl of 1-4 carbon atoms, —O-perfluoroalkyl of 1-4 carbon atoms, —$CONR_5R_6$, —$S(O)_nR_5$, —$OPO(OR_5)OR_6$, —$PO(OR_5)R_6$, —$OC(O)NR_5R_6$, —$C(O)NR_5OR_6$, —$COOR_5$, —$SO_3H$, —$NR_5R_6$, —$N[(CH_2)_2]_2NR_5$, —$NR_5COR_6$, —$NR_5COOR_6$, —$SO_2NR_5R_6$, —$NO_2$, —$N(R_5)SO_2R_6$, —$NR_5CONR_5R_6$, —$NR_5C(=NR_6)NR_5R_6$, —$NR_5C(=NR_6)N(SO_2)R_5R_6$, —$NR_5C(=NR_6)N(C=O)R_5R_6$, $NR_5C(=NR_6)N(SO_2R_5)R_6$, —$NR_5C(=NR_6)N(COR_5)R_6$, —$SO_2NHCOR_7$, —$CONHSO_2R_7$, tetrazol-5-yl, —$SO_2NHCN$, —$SO_2NHCONR_5R_6$, aryl of 6-12 carbon atoms, heteroaryl or heterocycloalkyl;
$R_5$ and $R_6$ are each, independently, hydrogen, alkyl of 1-6 carbon atoms, cycloalkyl of 3-6 carbon atoms, aryl of 6-12 carbon atoms, heteroaryl or heterocycloalkyl; or when $R_5$ and $R_6$ are taken together in —$NR_5R_6$ form a pyrrolidine, piperidine, morpholine, thiomorpholine, oxazolidine, thiazolidine, pyrazolidine, piperazine, or azetidine ring;
$R_7$ is alkyl of 1-6 carbon atoms, alkenyl of 2-6 carbon atoms, alkynyl of 2-6 carbon atoms, cycloalkyl of 3-6 carbon atoms, perfluoroalkyl of 1-4 carbon atoms, aryl of 6-12 carbon atoms, heteroaryl or heterocycloalkyl; and n is 0 to 2;
or a pharmaceutically acceptable salt thereof;
wherein the disease or disorder is rheumatoid arthritis, graft rejection, cachexia, inflammation, fever, insulin resistance, septic shock, congestive heart failure, inflammatory bowel disease or HIV infection.

2. The method of claim 1, wherein A is a phenyl or naphthyl.

3. The method of claim 2, wherein Z is O.

4. The method of claim 3, wherein $R_1$ and $R_2$ are hydrogen.

5. The method of claim 4, wherein $R_3$ is —$CH_2OH$ or methyl.

6. The method of claim 1, wherein the compound administered is
2-[(hydroxyamino)carbonyl]-6-methylphenyl 4-(2-butynyloxy)benzenesulfonate,
2-[(hydroxyamino)carbonyl]-6-methoxyphenyl 4-(2-butynyloxy)benzenesulfonate,
2-[(hydroxyamino)carbonyl]-4,6-diisopropylphenyl 4-(2-butynyloxy)benzenesulfonate,
2-[(hydroxyamino)carbonyl]-4-methylphenyl 4-(2-butynyloxy)benzenesulfonate; or
3-[(hydroxyamino)carbonyl]-2-naphthyl 4-(2-butynyloxy)benzenesulfonate; or
a pharmaceutically acceptable salt thereof.

7. The method of claim 2, wherein A is phenyl or naphthyl, each optionally independently mono-, di- or tri-substituted with alkyl of 1-6 carbon atoms or —$OR_5$, wherein each $R_5$ is independently alkyl of 1-6 carbon atoms.

8. The method of claim 7, wherein A is phenyl optionally independently mono- or di-substituted with methyl, isopropyl or methoxy, or A is naphthyl.

9. The method of claim 7, wherein Z is O.

10. The method of claim 9, wherein $R_1$ and $R_2$ are hydrogen.

11. The method of claim 10, wherein $R_3$ is —$CH_2OH$ or methyl.

* * * * *